US011497845B2

(12) United States Patent
Foley et al.

(10) Patent No.: US 11,497,845 B2
(45) Date of Patent: *Nov. 15, 2022

(54) TRANS ANAL IRRIGATION PLATFORM WITH BED MODULE

(71) Applicant: Hollister Incorporated, Libertyville, IL (US)

(72) Inventors: Adam J. Foley, Swords (IE); Stephen Collum, Castlebar (IE); Denise Gamblin, Leeds (GB); William K. Arnold, Gurnee, IL (US); Ruchi Seth, Libertyville, IL (US); Jerome A. Henry, Castlebar (IE); Malford E. Cullum, Grayslake, IL (US); George J. Cisko, Spring Grove, IL (US)

(73) Assignee: Hollister Incorporated, Libertyville, IL (US)

( * ) Notice: Subject to any disclaimer, the term of this patent is extended or adjusted under 35 U.S.C. 154(b) by 317 days.

This patent is subject to a terminal disclaimer.

(21) Appl. No.: 16/883,675

(22) Filed: May 26, 2020

(65) Prior Publication Data

US 2020/0316287 A1 Oct. 8, 2020

Related U.S. Application Data

(60) Division of application No. 15/322,960, filed as application No. PCT/US2015/039416 on Jul. 7, 2015, (Continued)

(51) Int. Cl.
*A61M 3/02* (2006.01)
*A61M 39/22* (2006.01)

(52) U.S. Cl.
CPC .......... *A61M 3/0295* (2013.01); *A61M 3/022* (2014.02); *A61M 3/027* (2013.01);
(Continued)

(58) Field of Classification Search
CPC .. A61M 3/027; A61M 3/0258; A61M 3/0287; A61M 3/0295; A61M 3/0208;
(Continued)

(56) References Cited

U.S. PATENT DOCUMENTS 1,004,103 A 9/1911 Tacey
1,317,851 A * 10/1919 Arnett ................. A61M 3/0283
604/34
(Continued)

FOREIGN PATENT DOCUMENTS

AT 369994 B 2/1983
DE 4114390 * 11/1992
(Continued)

OTHER PUBLICATIONS

Urinary Incontinence Applicance, Aids and Equipment, R.N.P. Carroll, retrieved on Apr. 3, 2014 from http://link.springer.com/chapter/10.1007/978-1-4471-1461-1_6# dated Dec. 31, 1992.
(Continued)

*Primary Examiner* — Theodore J Stigell
(74) *Attorney, Agent, or Firm* — Cook Alex Ltd.

(57) ABSTRACT

A trans anal irrigation device that can be used on a bed. The device includes a rectal catheter connected to an irrigation fluid supply. A waste collection bag is also connected to the catheter. The catheter may be insertable in a seat attached to a fluid supply line. A valve in one of the catheter or seat selectably allows or prevents fluid communication between the catheter and a waste collection bag. The catheter may include an inflationless cuff made of a flexible material that permits it to be inserted in the rectum to prevent leakage around the exterior of the catheter.

11 Claims, 11 Drawing Sheets

Related U.S. Application Data now Pat. No. 10,765,796, and a continuation of application No. PCT/US2014/053573, filed on Aug. 29, 2014.

(60) Provisional application No. 62/022,051, filed on Jul. 8, 2014, provisional application No. 62/022,075, filed on Jul. 8, 2014.

(52) U.S. Cl.
CPC ........ *A61M 3/0208* (2014.02); *A61M 3/0258* (2013.01); *A61M 3/0287* (2013.01); *A61M 39/22* (2013.01); *A61M 2205/502* (2013.01); *A61M 2205/75* (2013.01); *A61M 2205/8206* (2013.01); *A61M 2210/1064* (2013.01); *A61M 2210/1067* (2013.01)

(58) Field of Classification Search
CPC .................. A61M 3/022; A61M 39/22; A61M 2210/1064; A61M 2039/229; A61M 2205/502; A61M 2205/75; A61M 2205/8206; A61M 3/0202; A61M 3/0245
See application file for complete search history.

(56) References Cited

U.S. PATENT DOCUMENTS

| | | | |
|---|---|---|---|
| 1,566,061 | A | 12/1925 | Ziegler |
| 1,710,701 | A * | 4/1929 | Hertzberg ........... A61M 3/0283 604/41 |
| 1,853,202 | A | 4/1932 | Catlin |
| 2,345,275 | A | 3/1944 | Marvin |
| 2,691,373 | A * | 10/1954 | Bried .................. A61M 3/0233 604/248 |
| 3,042,039 | A | 7/1962 | Dahlstrom |
| 3,802,418 | A | 4/1974 | Clayton |
| 3,854,483 | A | 12/1974 | Powers |
| 3,889,676 | A | 6/1975 | Greene |
| 3,894,540 | A | 7/1975 | Bonner, Jr. |
| 3,910,274 | A | 10/1975 | Nolan |
| 3,934,722 | A | 1/1976 | Goldberg |
| 4,043,345 | A | 8/1977 | Kramann et al. |
| 4,109,659 | A | 8/1978 | Sheridan |
| 4,117,847 | A | 10/1978 | Clayton |
| 4,386,607 | A | 6/1983 | Miller |
| 4,842,580 | A * | 6/1989 | Ouelette ............. A61M 3/0212 604/246 |
| 4,874,363 | A | 10/1989 | Abell |
| 4,956,298 | A | 9/1990 | Diekmann |
| 5,019,056 | A | 5/1991 | Lee et al. |
| 5,149,326 | A | 9/1992 | Woodgrift et al. |
| 5,176,630 | A | 1/1993 | Shilling et al. |
| 5,217,114 | A | 6/1993 | Gadberry et al. |
| 5,225,165 | A | 7/1993 | Perlman |
| 5,405,319 | A | 4/1995 | Abell et al. |
| 5,413,561 | A | 5/1995 | Fischell et al. |
| 5,417,326 | A | 5/1995 | Winer |
| 5,868,265 | A | 2/1999 | Kobayashi |
| 5,881,774 | A | 3/1999 | Utterberg |
| 6,106,506 | A | 8/2000 | Abell et al. |
| 6,258,078 | B1 | 7/2001 | Thilly |
| 6,468,245 | B2 | 10/2002 | Alexanderson |
| 6,585,721 | B2 | 7/2003 | Fiore |
| 6,822,253 | B1 | 11/2004 | Martin et al. |
| 6,908,013 | B2 | 6/2005 | Thomson et al. |
| 6,984,226 | B1 | 1/2006 | Abell et al. |
| 7,120,487 | B2 | 10/2006 | Nelson |
| 7,438,704 | B1 | 10/2008 | Kawashima et al. |
| 7,546,952 | B2 | 6/2009 | Giusti |
| 7,571,804 | B2 | 8/2009 | Kjellmann Bruun et al. |
| 7,585,294 | B2 | 9/2009 | Jensen et al. |
| 7,614,514 | B2 | 11/2009 | Fuchs |
| 7,625,355 | B2 | 12/2009 | Yu |
| 7,682,353 | B2 | 3/2010 | Tanghoj |
| 7,717,284 | B2 | 5/2010 | Giusti |
| 7,748,550 | B2 | 7/2010 | Cho |
| 7,867,220 | B2 | 1/2011 | Tanghoj |
| 7,886,907 | B2 | 2/2011 | Murray et al. |
| 7,967,744 | B2 | 6/2011 | Kaye et al. |
| 8,137,309 | B2 | 3/2012 | Nishtala et al. |
| 8,172,101 | B2 | 5/2012 | Giusti |
| 8,181,778 | B1 | 5/2012 | van Groningen et al. |
| 8,230,993 | B2 | 7/2012 | Tanghoej |
| 8,231,589 | B2 | 7/2012 | Moeller-Jensen et al. |
| 8,282,624 | B2 | 10/2012 | Tanghoej et al. |
| 8,361,057 | B2 | 1/2013 | Tanghoej et al. |
| 8,398,615 | B2 | 3/2013 | Torstensen et al. |
| 8,434,639 | B2 | 5/2013 | Markert |
| 8,439,213 | B2 | 5/2013 | Goria et al. |
| 8,448,798 | B2 | 5/2013 | Groubert |
| 8,491,568 | B2 | 7/2013 | Schertiger et al. |
| 8,568,348 | B2 | 10/2013 | Vlodaver et al. |
| 8,574,206 | B2 | 11/2013 | Bjerregaard et al. |
| 8,579,115 | B2 | 11/2013 | Murphy et al. |
| 8,752,722 | B2 | 6/2014 | Kuhn et al. |
| 8,863,968 | B2 | 10/2014 | Giusti |
| 8,900,184 | B2 | 12/2014 | Gobel |
| 9,352,318 | B2 | 5/2016 | Giusti |
| 9,422,089 | B2 | 8/2016 | Wheeler |
| 10,765,796 | B2 * | 9/2020 | Foley .................. A61M 3/0287 |
| 2002/0019613 | A1 | 2/2002 | Alexandersen |
| 2003/0073963 | A1 | 4/2003 | Falconer |
| 2003/0073974 | A1 | 4/2003 | Falconer |
| 2004/0267198 | A1 | 12/2004 | Torstensen |
| 2005/0148954 | A1 | 7/2005 | Abell |
| 2006/0009732 | A1 | 1/2006 | Hardy |
| 2006/0142737 | A1 | 6/2006 | Tanghoj |
| 2006/0180585 | A1 | 8/2006 | Cunningham et al. |
| 2007/0073216 | A1 | 3/2007 | McAuliffe et al. |
| 2008/0033371 | A1 | 2/2008 | Updegraff et al. |
| 2008/0097384 | A1 | 4/2008 | Pacey |
| 2008/0289984 | A1 | 11/2008 | Raven |
| 2009/0054876 | A1 | 2/2009 | Borodulin |
| 2009/0166361 | A1 | 7/2009 | Lourenco |
| 2010/0106236 | A1 | 4/2010 | Nelson |
| 2010/0211050 | A1 | 8/2010 | Luther |
| 2010/0324540 | A1 | 12/2010 | Paulen et al. |
| 2011/0060317 | A1 | 3/2011 | Frojd |
| 2011/0224653 | A1 | 9/2011 | Torstensen |
| 2011/0282311 | A1 | 11/2011 | Nishtala |
| 2011/0302709 | A1 | 12/2011 | Taylor |
| 2012/0016318 | A1 | 1/2012 | Hoang et al. |
| 2012/0179144 | A1 | 7/2012 | Carleo |
| 2012/0271281 | A1 | 10/2012 | Schertiger |
| 2013/0068767 | A1 | 3/2013 | Fraser et al. |
| 2013/0134123 | A1 | 5/2013 | Fraser |
| 2013/0161343 | A1 | 6/2013 | Park et al. |
| 2013/0218136 | A1 | 8/2013 | Tanghoej et al. |
| 2013/0289537 | A1 | 10/2013 | Schertiger |
| 2013/0292286 | A1 | 11/2013 | Van Groningen |
| 2014/0005602 | A1 | 1/2014 | Andreen et al. |
| 2014/0262860 | A1 | 9/2014 | Hagel |
| 2014/0263436 | A1 | 9/2014 | Gelov et al. |
| 2014/0360896 | A1 | 12/2014 | Torstensen |
| 2016/0016703 | A1 | 1/2016 | Muhlemann |
| 2016/0023818 | A1 | 1/2016 | Gelov et al. |
| 2016/0059999 | A1 | 3/2016 | Fraser et al. |
| 2016/0228872 | A1 | 8/2016 | Giusti |

FOREIGN PATENT DOCUMENTS

| | | |
|---|---|---|
| DE | 4114390 A1 | 11/1992 |
| DE | 4114390 A1 | 11/1992 |
| DE | 20117438 U1 | 3/2002 |
| DE | 10213411 A1 | 10/2003 |
| DE | 20317135 U1 | 2/2004 |
| DE | 202005008071 U1 | 7/2005 |
| DE | 202005009946 U1 | 9/2005 |
| DE | 202006013663 U1 | 11/2006 |
| DE | 202010006267 U1 | 11/2010 |
| DE | 202010007433 U1 | 7/2011 |
| DE | 202011107025 | 3/2013 |
| DE | 202011107059 | 3/2013 |

(56) References Cited

FOREIGN PATENT DOCUMENTS

| | | |
|---|---|---|
| DE | 102013014483 A1 | 6/2014 |
| EP | 0041487 A | 12/1981 |
| EP | 0134630 A | 3/1985 |
| EP | 0861639 A2 | 9/1998 |
| EP | 0809520 B1 | 4/1999 |
| EP | 0996542 A1 | 5/2000 |
| EP | 1051984 A2 | 11/2000 |
| EP | 1180373 A2 | 2/2002 |
| EP | 1011754 B1 | 9/2004 |
| EP | 1466645 A2 | 10/2004 |
| EP | 1392575 B1 | 9/2005 |
| EP | 1593710 A1 | 11/2005 |
| EP | 1634554 A2 | 3/2006 |
| EP | 1638856 A1 | 3/2006 |
| EP | 1246655 B1 | 5/2006 |
| EP | 1434611 B1 | 6/2006 |
| EP | 1671663 A1 | 6/2006 |
| EP | 1303243 B1 | 1/2007 |
| EP | 1752175 A1 | 2/2007 |
| EP | 1752176 A1 | 2/2007 |
| EP | 1752177 A1 | 2/2007 |
| EP | 1039858 B1 | 5/2007 |
| EP | 1491223 B1 | 5/2007 |
| EP | 1878461 A1 | 1/2008 |
| EP | 1897579 A1 | 3/2008 |
| EP | 1897580 A1 | 3/2008 |
| EP | 1946785 A1 | 7/2008 |
| EP | 1946786 A1 | 7/2008 |
| EP | 1372755 B1 | 8/2008 |
| EP | 0915715 B1 | 9/2008 |
| EP | 1514572 B1 | 10/2008 |
| EP | 1531885 B1 | 10/2008 |
| EP | 1977778 A1 | 10/2008 |
| EP | 1982741 A2 | 10/2008 |
| EP | 2027832 A2 | 2/2009 |
| EP | 2042211 A1 | 4/2009 |
| EP | 2044963 A1 | 4/2009 |
| EP | 2060296 A1 | 5/2009 |
| EP | 2072075 A1 | 6/2009 |
| EP | 2106821 A1 | 10/2009 |
| EP | 2035292 B1 | 5/2010 |
| EP | 2251454 A2 | 11/2010 |
| EP | 2468326 A1 | 12/2010 |
| EP | 2211937 B1 | 7/2011 |
| EP | 2125070 B1 | 4/2012 |
| EP | 2452706 A2 | 5/2012 |
| EP | 2468319 A1 | 6/2012 |
| EP | 2005981 B1 | 9/2012 |
| EP | 1909864 B1 | 10/2012 |
| EP | 2504054 A1 | 10/2012 |
| EP | 2515985 A1 | 10/2012 |
| EP | 2158926 B1 | 5/2013 |
| EP | 2596831 A2 | 5/2013 |
| EP | 2242696 B1 | 6/2013 |
| EP | 2617316 A2 | 7/2013 |
| EP | 2638927 A2 | 9/2013 |
| EP | 2671601 A1 | 11/2013 |
| EP | 2671602 A1 | 12/2013 |
| EP | 2679259 A1 | 1/2014 |
| EP | 2679260 A1 | 1/2014 |
| EP | 2679261 A1 | 1/2014 |
| EP | 2682069 A1 | 1/2014 |
| EP | 2686054 A1 | 1/2014 |
| EP | 2703019 A1 | 3/2014 |
| EP | 2416819 B1 | 8/2014 |
| EP | 1752174 B1 | 9/2014 |
| EP | 2774648 A1 | 9/2014 |
| EP | 2576374 B1 | 9/2016 |
| FR | 2717676 A1 | 9/1995 |
| GB | 2031735 A | 4/1980 |
| GB | 2033231 A | 5/1980 |
| GB | 2322079 A | 8/1998 |
| GB | 2496900 A | 5/2013 |
| JP | 2001025473 | 1/2001 |
| KR | 20110101674 | 7/2012 |
| WO | WO 96-08219 A1 | 3/1996 |
| WO | WO 96-25188 A1 | 8/1996 |
| WO | WO 96-31250 A1 | 10/1996 |
| WO | WO 97-15335 A1 | 5/1997 |
| WO | WO 97-26937 A1 | 7/1997 |
| WO | WO 97/41811 A1 | 11/1997 |
| WO | WO 97-49441 A1 | 12/1997 |
| WO | WO 98-11932 A1 | 3/1998 |
| WO | WO 98-19729 A1 | 5/1998 |
| WO | WO 98-20722 A2 | 5/1998 |
| WO | WO 98-23312 A1 | 6/1998 |
| WO | WO 99-30652 A1 | 6/1999 |
| WO | WO 99-30761 A1 | 6/1999 |
| WO | WO 99-42155 A2 | 8/1999 |
| WO | WO 99-59656 A1 | 11/1999 |
| WO | WO 00-16843 A1 | 3/2000 |
| WO | WO 00-30575 A1 | 6/2000 |
| WO | WO 00-47494 A1 | 8/2000 |
| WO | WO 01-43807 A1 | 6/2001 |
| WO | WO 01-49345 A1 | 7/2001 |
| WO | WO 01-60255 A1 | 8/2001 |
| WO | WO 02-07668 A1 | 1/2002 |
| WO | WO 02-13887 A1 | 2/2002 |
| WO | WO 02-060361 A2 | 8/2002 |
| WO | WO 02-074363 A2 | 9/2002 |
| WO | WO 02-080843 A2 | 10/2002 |
| WO | WO 03-001994 A1 | 1/2003 |
| WO | WO 03-008028 A2 | 1/2003 |
| WO | WO 03-008029 A2 | 1/2003 |
| WO | WO 03-022561 A1 | 3/2003 |
| WO | WO 03-030967 A1 | 4/2003 |
| WO | WO 03-030968 A1 | 4/2003 |
| WO | WO 03-030969 A1 | 4/2003 |
| WO | WO 03-045487 A2 | 6/2003 |
| WO | WO 03-061732 A2 | 7/2003 |
| WO | WO 03-063668 A1 | 8/2003 |
| WO | WO 03-092779 A1 | 11/2003 |
| WO | WO 03-097237 A2 | 11/2003 |
| WO | WO 2004-006993 A1 | 1/2004 |
| WO | WO 2004-021890 A1 | 3/2004 |
| WO | WO 2004-032750 A1 | 4/2004 |
| WO | WO 2004-035123 A1 | 4/2004 |
| WO | WO 2004-050155 A1 | 6/2004 |
| WO | WO 2004-054446 A1 | 7/2004 |
| WO | WO 2004-060259 A2 | 7/2004 |
| WO | WO 2004-103153 A2 | 12/2004 |
| WO | WO 2004-112712 A2 | 12/2004 |
| WO | WO 2005-003725 A1 | 1/2005 |
| WO | WO 2005-004964 A1 | 1/2005 |
| WO | WO 2005-004970 A1 | 1/2005 |
| WO | WO 2005-014055 A2 | 2/2005 |
| WO | WO 2005-032617 A2 | 4/2005 |
| WO | WO 2006-005349 A1 | 1/2006 |
| WO | WO 2006-010556 A1 | 2/2006 |
| WO | WO 2006-015223 A2 | 2/2006 |
| WO | WO 2006/017439 A2 | 2/2006 |
| WO | WO 2006-024205 A1 | 3/2006 |
| WO | WO 2006/044249 A2 | 4/2006 |
| WO | WO 2006/044621 A2 | 4/2006 |
| WO | WO 2006/045809 A1 | 5/2006 |
| WO | WO 2006/121183 A1 | 11/2006 |
| WO | WO 2006-135934 A2 | 12/2006 |
| WO | WO 2007/005851 A2 | 1/2007 |
| WO | WO 2007/022223 A2 | 2/2007 |
| WO | WO 2007/038988 A1 | 4/2007 |
| WO | WO 2007/050685 A2 | 5/2007 |
| WO | WO 2007/081264 A1 | 7/2007 |
| WO | WO 2007/082540 A1 | 7/2007 |
| WO | WO 2007-103995 A2 | 9/2007 |
| WO | WO 2007/106356 A2 | 9/2007 |
| WO | WO 2007/106431 A2 | 9/2007 |
| WO | WO 2007/111891 A2 | 10/2007 |
| WO | WO 2007/121137 A2 | 10/2007 |
| WO | WO 2008/024136 A1 | 2/2008 |
| WO | WO 2008/030999 | 3/2008 |
| WO | WO 2008/039910 A2 | 4/2008 |
| WO | WO 2008-048856 A2 | 4/2008 |
| WO | WO 2008-058160 A2 | 5/2008 |
| WO | WO 2008-087220 A1 | 7/2008 |

(56) References Cited

FOREIGN PATENT DOCUMENTS

| | | |
|---|---|---|
| WO | WO 2008-087221 A2 | 7/2008 |
| WO | WO 2008/089081 A1 | 7/2008 |
| WO | WO 2008/090551 A2 | 7/2008 |
| WO | WO 2008/137353 A1 | 11/2008 |
| WO | WO 2009/010975 A1 | 1/2009 |
| WO | WO 2009-015152 A1 | 1/2009 |
| WO | WO 2009-017541 A1 | 2/2009 |
| WO | WO 2009-056906 A1 | 5/2009 |
| WO | WO 2009/066163 A1 | 5/2009 |
| WO | WO 2011-023196 A1 | 8/2009 |
| WO | WO 2009-128109 A1 | 10/2009 |
| WO | WO 2009/139878 A1 | 11/2009 |
| WO | WO 2009-144028 A1 | 12/2009 |
| WO | WO 2009-153973 A1 | 12/2009 |
| WO | WO 2010/006620 A1 | 1/2010 |
| WO | WO 2010-047501 A2 | 4/2010 |
| WO | WO 2010-057208 A1 | 5/2010 |
| WO | WO 2010-077980 A1 | 7/2010 |
| WO | WO 2010-115430 A1 | 10/2010 |
| WO | WO 2010-115431 A2 | 10/2010 |
| WO | WO 2010-126586 A1 | 11/2010 |
| WO | WO 2010/130261 A1 | 11/2010 |
| WO | WO 2011/011023 | 1/2011 |
| WO | WO 2011-012323 A1 | 2/2011 |
| WO | WO 2011-019359 A1 | 2/2011 |
| WO | WO 2011-026929 A | 3/2011 |
| WO | WO 2011-034911 A1 | 3/2011 |
| WO | WO 2011-075581 A1 | 6/2011 |
| WO | WO 2011/079129 A1 | 6/2011 |
| WO | WO 2011-105644 A1 | 9/2011 |
| WO | WO 2011/109393 A1 | 9/2011 |
| WO | WO 2011-139498 A1 | 11/2011 |
| WO | WO 2011/147803 A1 | 12/2011 |
| WO | WO 2012/006629 A2 | 1/2012 |
| WO | WO 2012/013662 A1 | 2/2012 |
| WO | WO 2012/016179 A1 | 2/2012 |
| WO | WO 2012/016570 A2 | 2/2012 |
| WO | WO 2012/016571 A2 | 2/2012 |
| WO | WO 2012/079590 A1 | 6/2012 |
| WO | WO 2012/085107 A2 | 6/2012 |
| WO | WO 2012/110755 A2 | 8/2012 |
| WO | WO 2012-120456 A2 | 9/2012 |
| WO | WO 2012/134804 A1 | 10/2012 |
| WO | WO 2012/154946 A1 | 11/2012 |
| WO | WO 2012/156478 A1 | 11/2012 |
| WO | WO 2012-164559 A1 | 12/2012 |
| WO | WO 2012/166045 A1 | 12/2012 |
| WO | WO 2012/166967 A1 | 12/2012 |
| WO | WO 2013-026564 A1 | 2/2013 |
| WO | WO 2013-026565 A1 | 2/2013 |
| WO | WO 2013/029620 A1 | 3/2013 |
| WO | WO 2013/029621 A1 | 3/2013 |
| WO | WO 2013/029622 A1 | 3/2013 |
| WO | WO 2013/075725 A1 | 5/2013 |
| WO | WO 2013-076446 A1 | 5/2013 |
| WO | WO 2013/083137 A1 | 6/2013 |
| WO | WO 2013-090778 A1 | 6/2013 |
| WO | WO 2013/098190 A1 | 7/2013 |
| WO | WO 2013/105091 A1 | 7/2013 |
| WO | WO 2013-163364 A1 | 10/2013 |
| WO | WO 2013-182593 A1 | 12/2013 |
| WO | WO 2013/184158 A1 | 12/2013 |
| WO | WO 2014-001292 A1 | 1/2014 |
| WO | WO 2014-001313 A1 | 1/2014 |
| WO | WO 2014-001322 A1 | 1/2014 |
| WO | WO 2014/062225 A1 | 4/2014 |
| WO | WO 2014/063711 A1 | 5/2014 |
| WO | WO 2014-064414 A1 | 5/2014 |
| WO | WO 2014/074142 A1 | 5/2014 |
| WO | WO 2014/074147 A1 | 5/2014 |
| WO | WO 2014/081859 A1 | 5/2014 |
| WO | WO 2014/085597 A1 | 6/2014 |
| WO | WO 2014-089278 A1 | 6/2014 |
| WO | WO 2014/093056 A1 | 6/2014 |
| WO | WO 2014/139767 | 9/2014 |
| WO | WO 2014/140328 A1 | 9/2014 |
| WO | WO 2014/142895 A1 | 9/2014 |
| WO | WO 2014/142917 A1 | 9/2014 |
| WO | WO 2014/142923 A1 | 9/2014 |
| WO | WO 2014/142930 A1 | 9/2014 |
| WO | WO 2014/144714 | 9/2014 |
| WO | WO 2014/145211 A2 | 9/2014 |
| WO | WO 2014/147620 A1 | 9/2014 |
| WO | WO 2014/149276 A1 | 9/2014 |
| WO | WO 2014/159869 A2 | 10/2014 |
| WO | WO 2014/165046 A1 | 10/2014 |
| WO | WO 2014/176486 A1 | 10/2014 |
| WO | WO 2014/176867 A1 | 11/2014 |
| WO | WO 2015/184365 | 12/2015 |

OTHER PUBLICATIONS

International Search Report dated Sep. 25, 2015, for International Application No. PCT/US2015/039416.

* cited by examiner

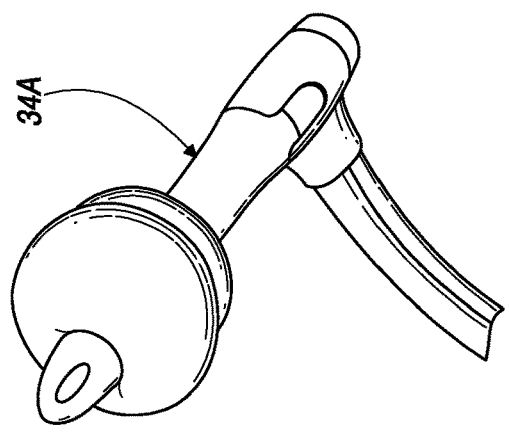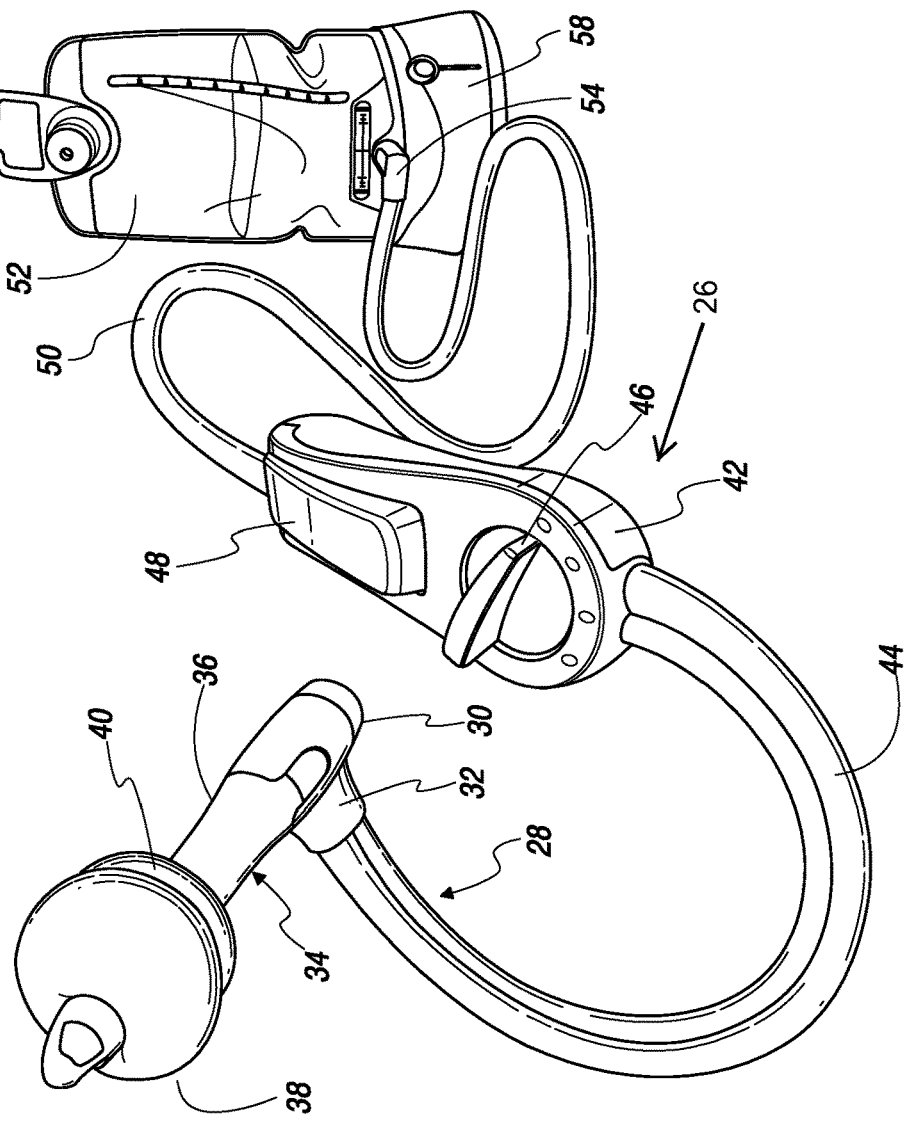

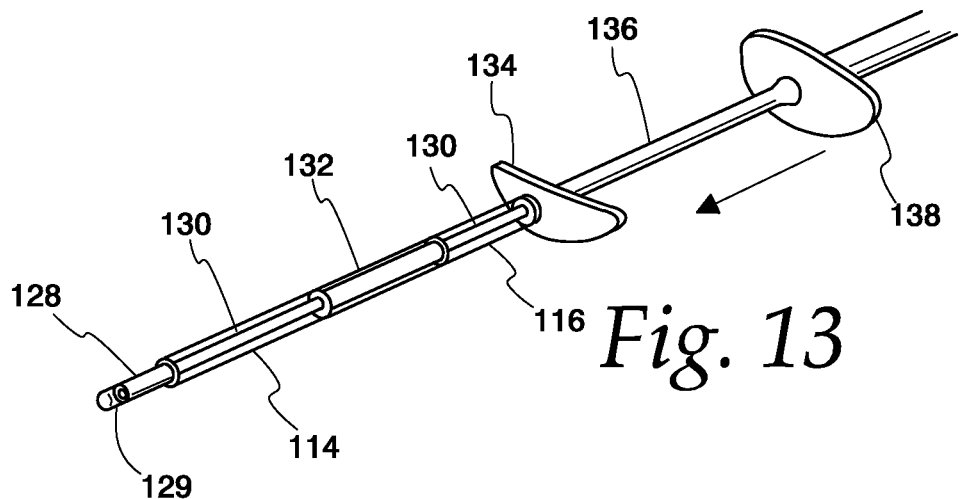
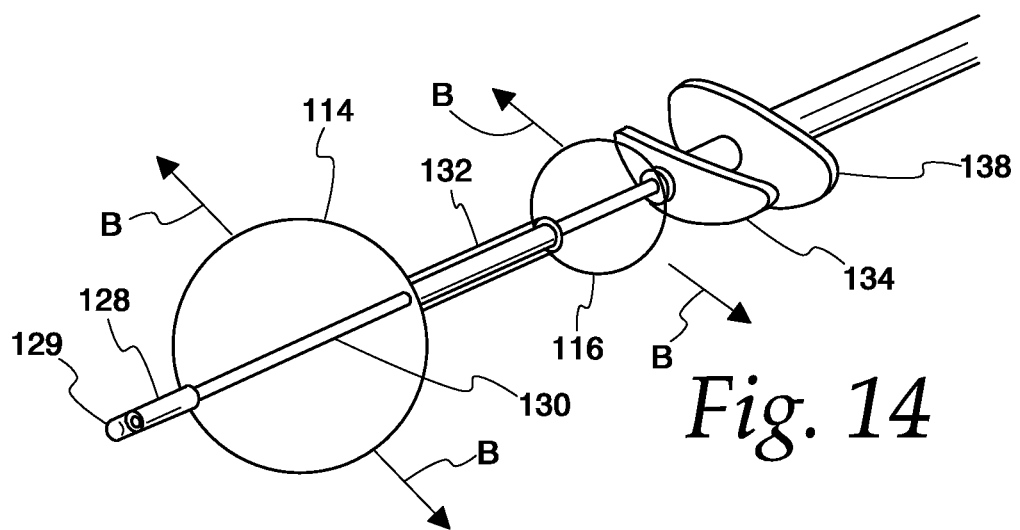

TRANS ANAL IRRIGATION PLATFORM WITH BED MODULE

CROSS REFERENCE TO RELATED APPLICATIONS

The present application is a divisional application of U.S. application Ser. No. 15/322,960, filed Dec. 29, 2016, which is a National Stage Entry of International Application No. PCT/US2015/039416, filed Jul. 7, 2015, which claims priority to and the benefit of U.S. Provisional Application Ser. No. 62/022,051, filed Jul. 8, 2014; PCT Application Serial No. PCT/US14/53573, filed Aug. 29, 2014; and U.S. Provisional Application Ser. No. 62/022,075, filed Jul. 8, 2014, the disclosures of which are hereby incorporated herein by reference.

FIELD OF THE DISCLOSURE

The present disclosure is directed to trans anal irrigation (TAI) devices, methods and systems.

BACKGROUND

Many individuals suffering spinal cord injury (SCI) and other medical conditions (e.g. Cauda Equina, MS, Spina Bifida, and Chronic Constipation) will need to avail themselves of bowel management treatments alongside their bladder management program. In terms of SCI users, the issues of independence, dexterity and ease of use are important needs that should be addressed by a bowel management program. Users can avail themselves of various solutions such as pharmacological treatments such laxatives or suppositories, digital stimulation, diet control and others, with the aim of having a regular bowel management routine without constipation or fecal incontinence. This concept will focus on trans anal irrigation (TAI) which is a solution for use in bowel care. TAI is the delivery of water into the colon to flush the system of stool and create pseudo-continence for the end user. Systems currently on the market allow the user to utilize a product over the toilet or in a commode/shower chair to introduce water into the bowel through a rectal catheter (in the form of rectal balloons/cones). The user will introduce an amount of water into the bowel (typically 500-700 mL) in order to flush out stool located in the bowel passage. The user will introduce the water, wait for a period of time, e.g., 30+ minutes, and allow gravity to flush the water and stool out of the body. The user can then have peace of mind through use of the product.

However, not all patients are able to utilize a toilet in the manner described above. The present invention is directed to TAI devices for patients who are confined to a bed or the like.

SUMMARY

Unlike currently available TAI solutions, our TAI platform delivers a bowel irrigation solution that can benefit patients with neurogenic bowel dysfunction of all dexterity levels and the ability to perform bowel irrigation on the bed. Caregivers have the option of using this system with patients of limited to greatly reduced dexterity, which provides great flexibility in providing care. End-users will prefer the ease of use of the controls and body interface compared to other options while finding our product intuitive, comfortable and safe. Easy to slide controls guide the automated dispensing of the water—no more difficult seals or hard-to-manipulate controls.

The TAI platform of the present disclosure addresses users such as those having neurogenic bowel dysfunction sufferers including MS, SB, SCI, partial paraplegics, full paraplegics, partial tetraplegics (usually patients that can self-catheterize) plus full tetraplegics (with a caregiver). There is also potential for use in hospitals' pre-surgery for bowel emptying. Such users have the following needs:

To be able to comfortably perform bowel management anywhere, e.g., on the bed vs. in the bathroom, home vs. public toilet, etc. The present disclosure addresses this need by allowing people to perform their bowel management routine on a bed and to utilize irrigation and gain the benefits it can bring.

To be able to empty a user's bowels without requiring digital stimulation or manual evacuation. The present disclosure addresses this need by providing TAI that can reduce the need for digital interventions.

To be able to stimulate a bowel movement, especially when constipated, and always get a good result, i.e., stool not too hard or soft. The present disclosure addresses this need by providing TAI that is effective at dealing with constipation and high blockages.

To be able to easily and confidently perform anal irrigation, i.e., insert and keep bowel catheter in place, know how to use it correctly, etc. The present disclosure addresses this need by providing a bed module that is simple to use and has features to reduce waste, clean up and odors.

The present disclosure provides a closed irrigation system which has advantages over TAI devices that have to be conducted over a toilet during use due to waste issues.

This consistent system maintains a routine bowel management program. It provides a system that can be utilized from a lying position in the bed. It is easier to use than prior products. Patients with limited dexterity will have less difficulty with the controls. It is the most intuitive TAI product. Patients will experience a less confusing set-up and use of the product resulting in fewer accidents. When assisted by a caregiver, the product may be used with patients of any dexterity level.

BRIEF DESCRIPTION OF THE DRAWINGS

FIG. 8 is a perspective view of an alternate embodiment of a toilet module having a disposable hybrid catheter.

FIG. 9 is a perspective view of an alternate embodiment of a catheter for use with the system of FIG. 8.

FIG. 13 is an enlarged perspective view of an alternate rectal catheter suitable for use in connection with various TAI systems, such as that of FIG. 12, with the catheter in its non-deployed or retracted condition.

FIG. 14 is an enlarged perspective view of the rectal catheter of FIG. 13 with the catheter in its deployed or extended condition.

DETAILED DESCRIPTION OF THE EMBODIMENTS

Figure 1:
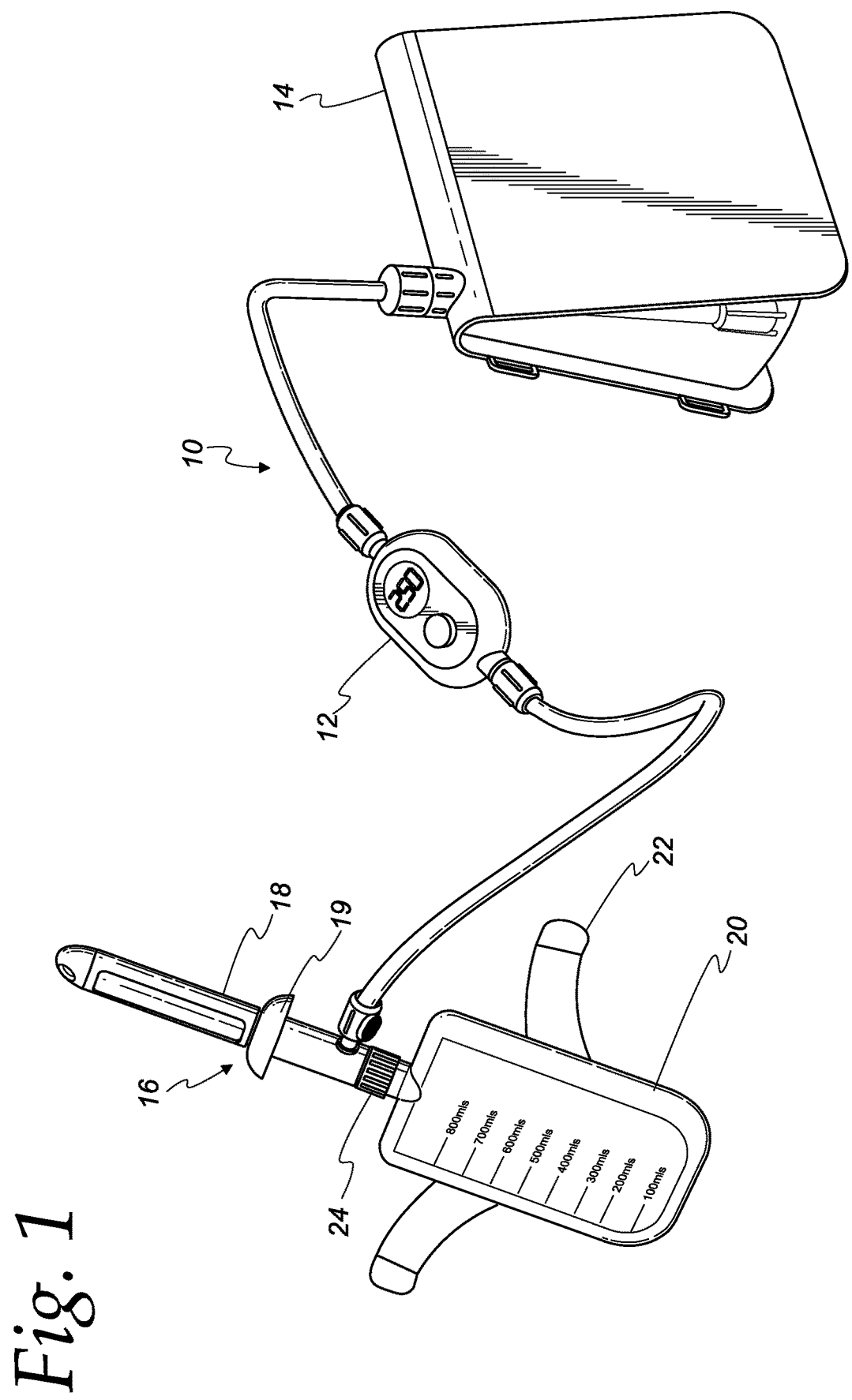
FIG. 1 is a perspective view of the TAI platform of the present disclosure.
Figure 2:
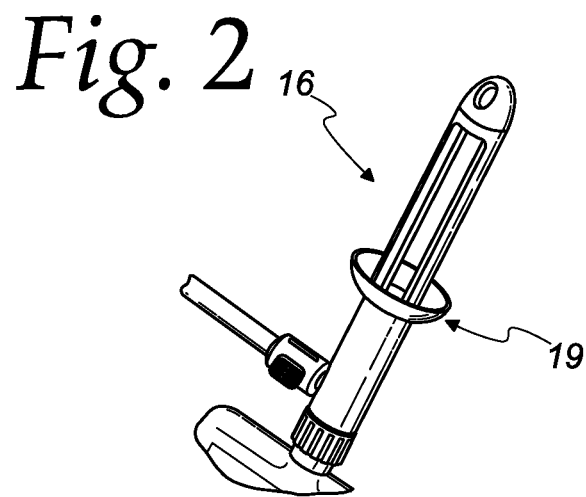
FIG. 2 is a perspective view of the bed module's rectal catheter.
Figure 3A:
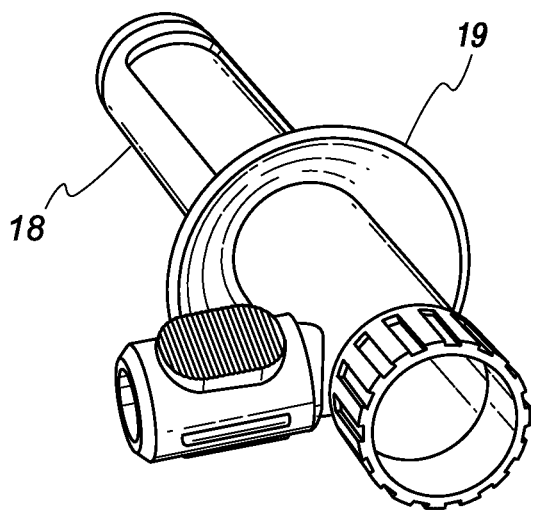
FIGS. 3a and 3b are perspective views of the bed module's rectal catheter.
Figure 3B:
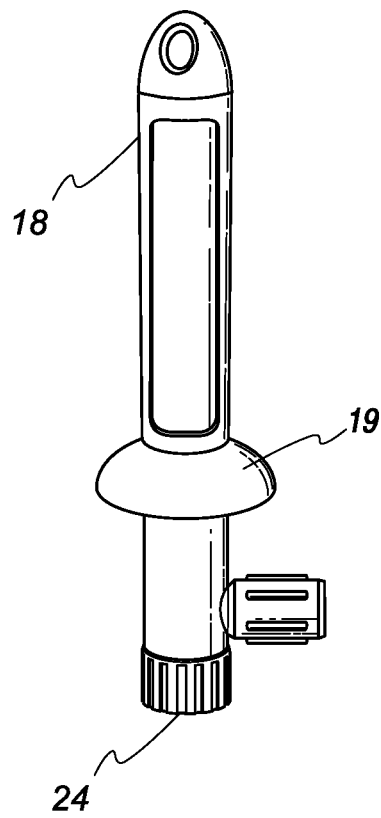
Figure 4:
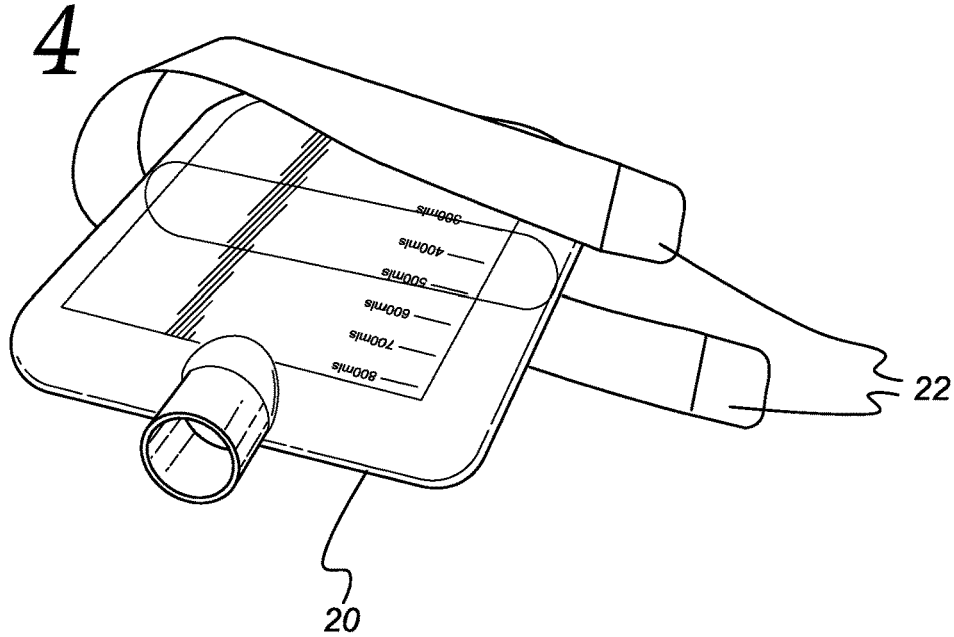
FIG. 4 is a perspective view of the closed collection bag.

FIGS. 1 and 2 detail an overview of TAI platform 10 with the bed module system. Note that the bed system will be attached to the appropriate controller 12 and water management solution 14 to provide irrigation with an attached bed module head 16. The bed module head is attached to the irrigation platform to adapt the design for bed use. A rectal catheter 18 features soft insertion tip and an inflationless retention cuff 19. A waste collection bag 20 captures and contains all fecal matter. The waste collection bag 20 may feature straps 22 to aid placement and carbon filters to control odors. A user will irrigate as normal through the catheter 18 and, when appropriate, open a valve 24 at the bottom of the device to release waste into the collection bag 20. The single use components of the bed system are the head 16 and the collection bag 20.

Benefits of the design include that it enables irrigation to be offered to people with high injuries. It allows for an existing irrigation routine to be maintained when a patient is in hospital or otherwise bed-bound.

Use of the platform is as follows. The irrigation system with a collection bag enables use on a bed. The simplicity and intuitiveness of the battery-powered system bring significant benefits to those users who perform their routine on the bed with the assistance of a caregiver. This concept opens up irrigation to those with high-level injuries. A rectal catheter with cuff and closed waste collection bag is connected to irrigation sources and then inserted into the anus. An anatomically shaped pad helps to secure the catheter in place. Water is passed into the large intestine through gravity or a motorized or pressure pump. After a prescribed time, a user will turn the valve 24 at the bottom of the rectal catheter to open the catheter section and to release waste water and contained stool into the collection bag 20. At the conclusion of the process the rectal catheter and connected collection bag are removed and disposed.

Figure 5:
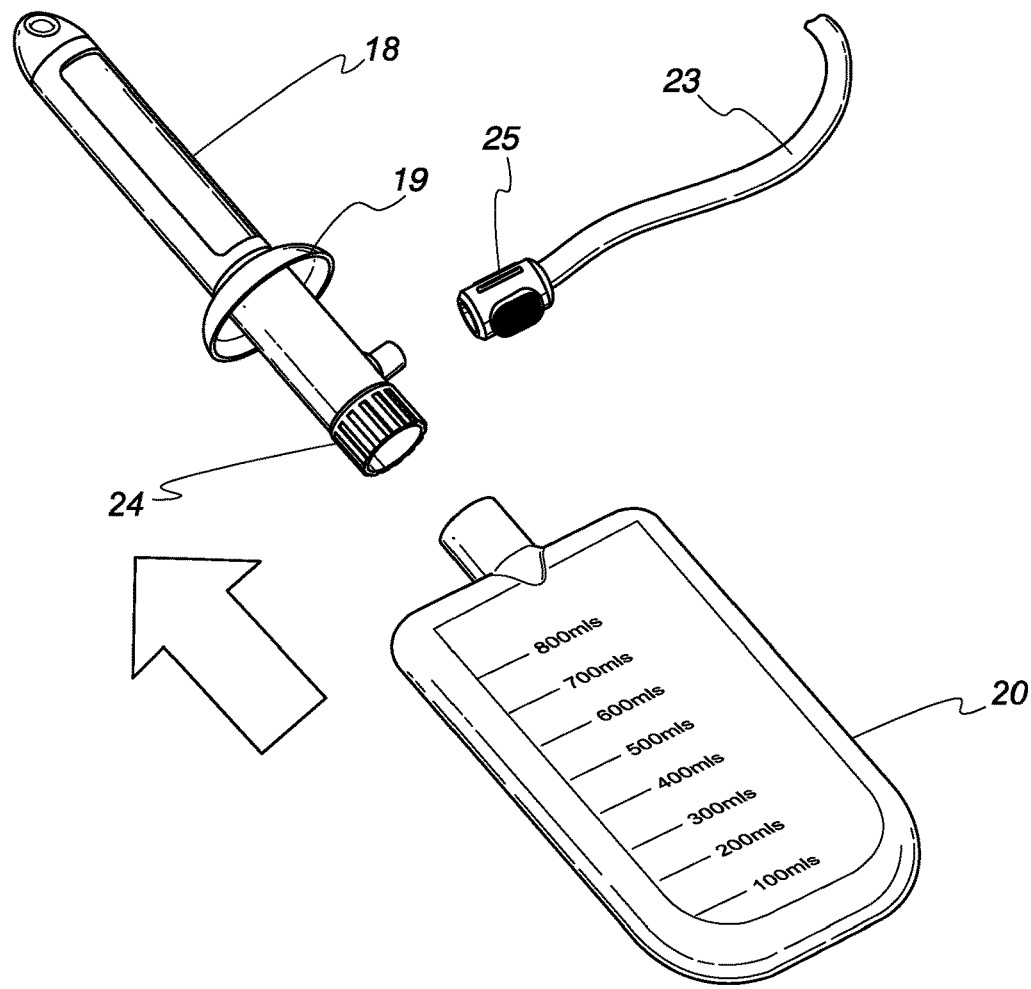
FIG. 5 is a perspective view of the setup process.
Figure 6:
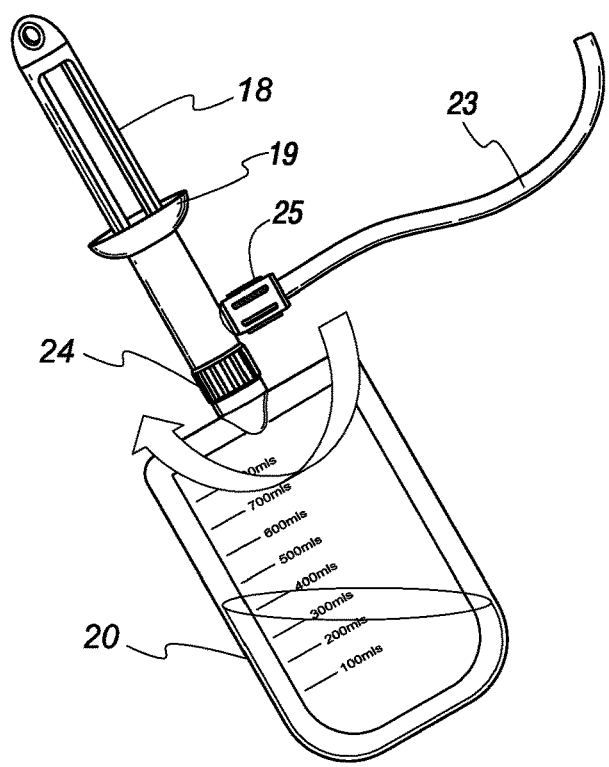
FIG. 6 is a perspective view showing the valve operation.
Figure 7:
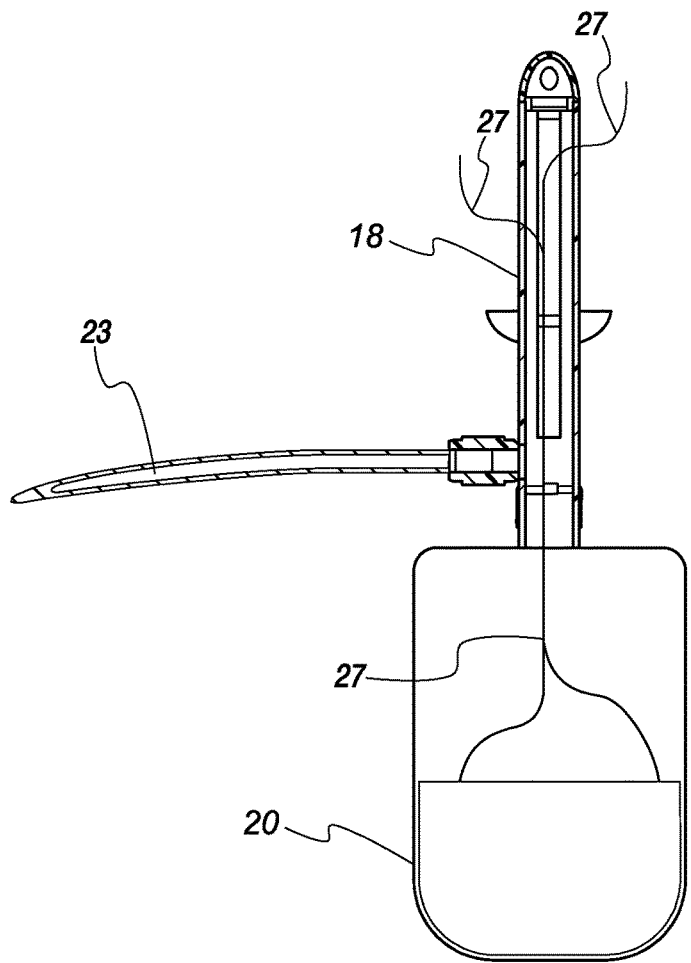
FIG. 7 is a schematic representation of the collection process.

FIGS. 3-7 illustrate the various components as shown in the bed module and set up. The bed module has a bed modular catheter 18 with a soft insertion tip, retention cuff 19, twist valve ports 24 to enable easy-to-use opening and operation. The closed collection bag 20 is connected to the bed module head and is a collection bag for clean containment of waster liquid expelled from the rectum. Straps 22 and carbon filters maybe used to improve performance of product. As seen in FIG. 5, the user will connect the bed module's rectal catheter 18 to the collection bag 20. The bed module with containing bag will be connected to the relevant irrigation source 14 (FIG. 1) through a connector 21 (FIG. 5). Irrigation fluid supply line 23 may have a connector 25 which is engageable with the connector 19 on the catheter 18. The user will perform irrigation as normal through the eyelets on the bed module, loading water into the rectum. The retention cuff 19 will keep the device in place and prevent leakage around the outside of the catheter.

Closed collection is as follows. When the desired level of water is inserted into the rectum the user will twist valve 24. The valve on the bed module will open an internal section and pathway, allowing waste water to flow from the bowel through the lumen in the catheter and into the collection bag, as schematically indicated at 27 in FIG. 7. The collection bag will feature non-return valves containing all expelled waste. The user will remove the catheter and attached bag and dispose of these items and the waste.

The retention device could be self-lubricating. The fecal matter collection is separate from the water reservoir chamber. The catheter could have a Velcro strap to secure the system to a patient. The system could be used to deliver medications. Carbon filters can be contained in the waste collection bag removing any associated odors. The waste collection bag could be made of flushable or bio-degradable materials aiding in disposal.

FIG. 8 illustrates an alternate TAI platform 26. It has an irrigation head 28 that includes a seat 30 and a tube attachment fitting 32 that adjoins a side of the seat 30 at a 90° angle that deters over-insertion of the catheter. The head 28 further incorporates a disposable hybrid catheter 34. The catheter 34 can be inserted into and removed from the seat 30. The hybrid catheter 34 has a barrel 36. Inside the barrel are two or more lumens for passage of irrigation water and waste, respectively. Alternately there may be a third lumen used to inflate a balloon 38 near the tip of the barrel. The balloon is shown inflated in FIG. 8. Immediately beneath the balloon is a non-inflatable cuff 40. The cuff is made of soft, pliable material such as silicone. The balloon 38 is inflated after it has been inserted into the rectum to hold the catheter in place. The balloon may be inflated either by water or by air. The non-inflatable cuff is also inserted into the rectum during use. It serves to prevent leakage around the exterior of the barrel. FIG. 9 shows an alternate form of the catheter at 34A. This version deletes the non-inflatable cuff 40 and relies on the balloon 38 for retention and sealing.

The TAI platform 26 further includes a control unit 42 that is connected to the irrigation head 28 by first tubing 44. First tubing 44 extends from the control unit 42 to the attachment fitting 32 and has dual lumens, one for balloon inflation (with either air or water) and one for irrigation fluid. The control unit 42 has an inflation/irrigation control knob 46 that directs irrigation fluid to the appropriate lumen in the barrel 36 of the catheter 34. A separate button 48 governs the on/off condition of the water pump. A second piece of tubing 50 provides fluid communication between the control until 42 and a water reservoir 52. A robust reservoir connection 54 joins the second tubing and water reservoir. The reservoir 52 may be collapsible for storage. It has a broad base that allows it to be free standing. A handle 56 may be included to allow the reservoir to be hung on a hook or carried. A fluid temperature indicator may be incorporated in the reservoir. A battery-operated pump 58 may interface with the reservoir bag. The pump has a compact size for storage and travel.

Figure 10:
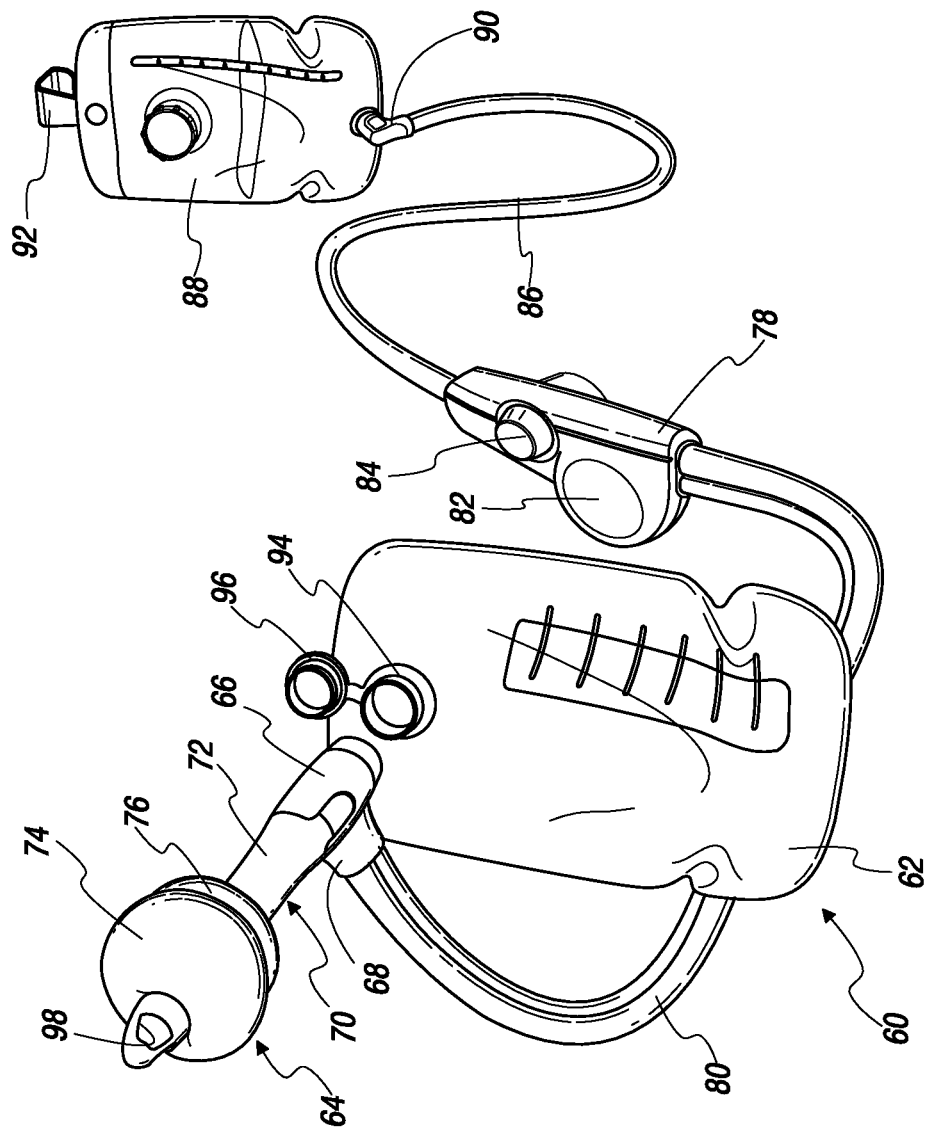
FIG. 10 is a perspective view of an alternate embodiment of a bed module having a disposable hybrid catheter.

The TAI platform 26 is intended for use with patients who are able to access a toilet such that waste material is collected in the toilet. In situations where use of a toilet is not possible or convenient a bed module TAI platform such as shown at 60 in FIG. 10 may be utilized. Platform 60 is similar in many ways to platform 26 but with the addition of a collection bag 62 that is removably connectable to the seat of the irrigation head. The collection bag 62 receives discharged waste through the catheter for subsequent disposal.

Figure 11:
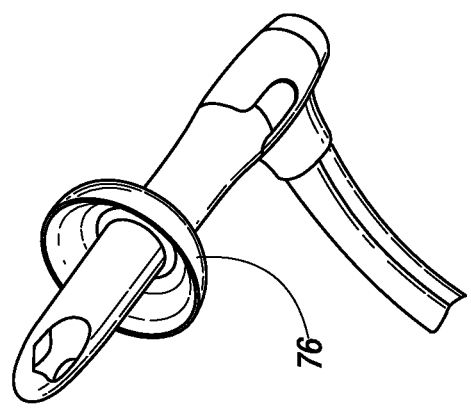
FIG. 11 is a perspective view of an alternate embodiment of a catheter for use with the system of FIG. 10.

Looking at alternate TAI platform 60 in greater detail, it has an irrigation head 64 that includes a seat 66 and a tube attachment fitting 68 that adjoins a side of the seat 66 at a 90° angle that deters over-insertion of the catheter. The head 64 further incorporates a disposable hybrid catheter 70. The catheter 70 can be inserted into and removed from the seat 66. The hybrid catheter 70 has a barrel 72. Inside the barrel are two or more lumens for passage of irrigation water and waste, respectively. Alternately there may be a third lumen used to inflate a balloon 74 near the tip of the barrel. The balloon is shown inflated in FIG. 10 and uninflated in FIG. 11. Immediately beneath the balloon is a non-inflatable cuff 76. The cuff is made of soft, pliable material such as silicone. The balloon 74 is inflated after it has been inserted into the rectum to hold the catheter in place. The balloon may be inflated either by water or by air. The non-inflatable cuff 76 is also inserted into the rectum during use. It serves to prevent leakage around the exterior of the barrel.

The TAI platform 60 further includes a control unit 78 that is connected to the irrigation head 64 by first tubing 80. First tubing 80 extends from the control unit 78 to the attachment fitting 68 and has dual lumens, one for balloon inflation (with either air or water) and one for irrigation fluid. The control unit 78 has an inflation/irrigation control knob 82 that directs irrigation fluid to the appropriate lumen in the barrel 72 of the catheter 70. A separate button 84 governs the on/off condition of the water pump. A second piece of tubing 86 provides fluid communication between the control until 78 and a water reservoir 88. A robust reservoir connection 90 joins the second tubing and water reservoir. The reservoir 88 may be collapsible for storage. It has a broad base that allows it to be free standing. A handle 92 may be included to allow the reservoir to be hung on a hook or carried. A fluid temperature indicator may be incorporated in the reservoir. This reservoir uses a gravity feed supply, although a pump as shown at 58 could alternately be used. The reservoir has a compact size for storage and travel.

The collection bag 62 has a connector 94 that is closable by a cap 96. When the cap is removed the connector can be attached in fluid communication with the distal end of the seat 66. With the collection bag so attached waste irrigation fluid and stool are allowed to flow from the rectum into a port 98 on the tip of the catheter barrel 72 and from there through a lumen of the barrel and into the collection bag. A valve may be incorporated in the seat to open and close the waste lumen in the catheter. The collection bag may be opaque with integrated odor control.

Figure 12:
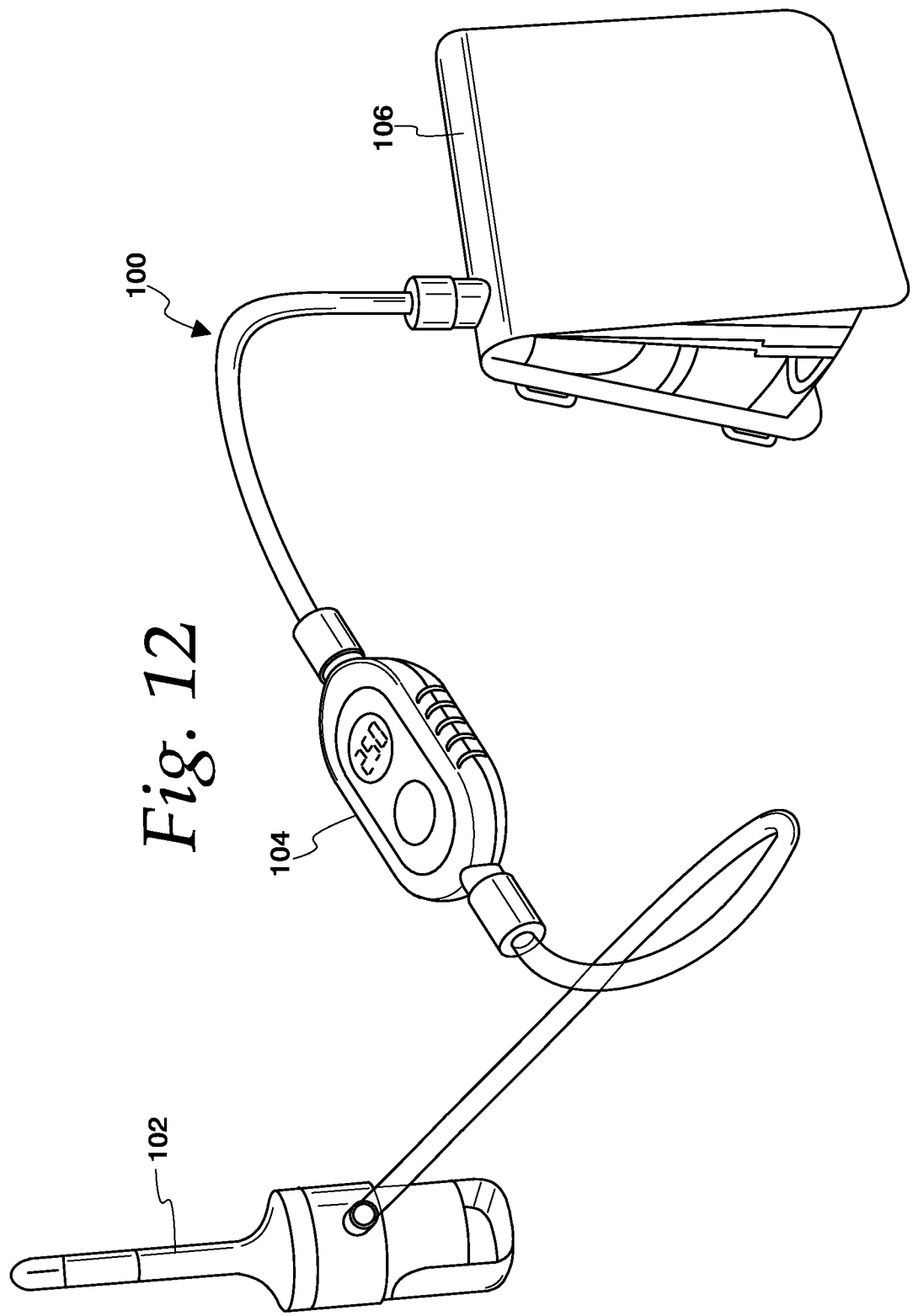
FIG. 12 is a perspective view of a further alternate embodiment of a TAI pressure system of the present disclosure.

FIG. 12 shows an overview of the TAI platform solution 100 of the present disclosure. Body interface 102 features a pre-filled inflation balloon for secure retention and is intuitive, provides one handed-insertion and removal of the device in a single use option. The user interface/controller 104 features a battery-powered pump with a large ON/OFF switch controller, Simple, intuitive controls and an easy-to-read volume display indicate to the user the amount of flow in milliliters of water loaded into the bowel. The water management device 106 details a water bag with a robust design and a siphon pump that doesn't need to be elevated, and has easy-to-open connections. This enables an easy-to-use and train design, an ergonomic and less bulky design for storage and a device that is intuitive and logical to understand with the simple ON/OFF switch for hands free pumping.

The embodiment of FIG. 12 provides an intuitive, battery-powered irrigation system. The body-interface is inserted and inflated in a simple motion and the easy-to-read digital interface allow the user to easily control the flow rate and volume regardless of hand function. The disposable balloon catheter is removed from packaging, connected to the system and inserted into the anus. The rectal IC is preloaded with air or gel similar to that of a syringe device.

An in-line digital controller allows the user to customize the flow rate. The rectal balloon is retracted and deflated and the catheter is removed from the anus, thus facilitating evacuation of fecal matter. The motorized system enables hands-free, controlled pumping of water into the body in a simple easy-to-use system. The rectal catheter is disposed of and the controller and pump are retained for future use.

Figure 15:
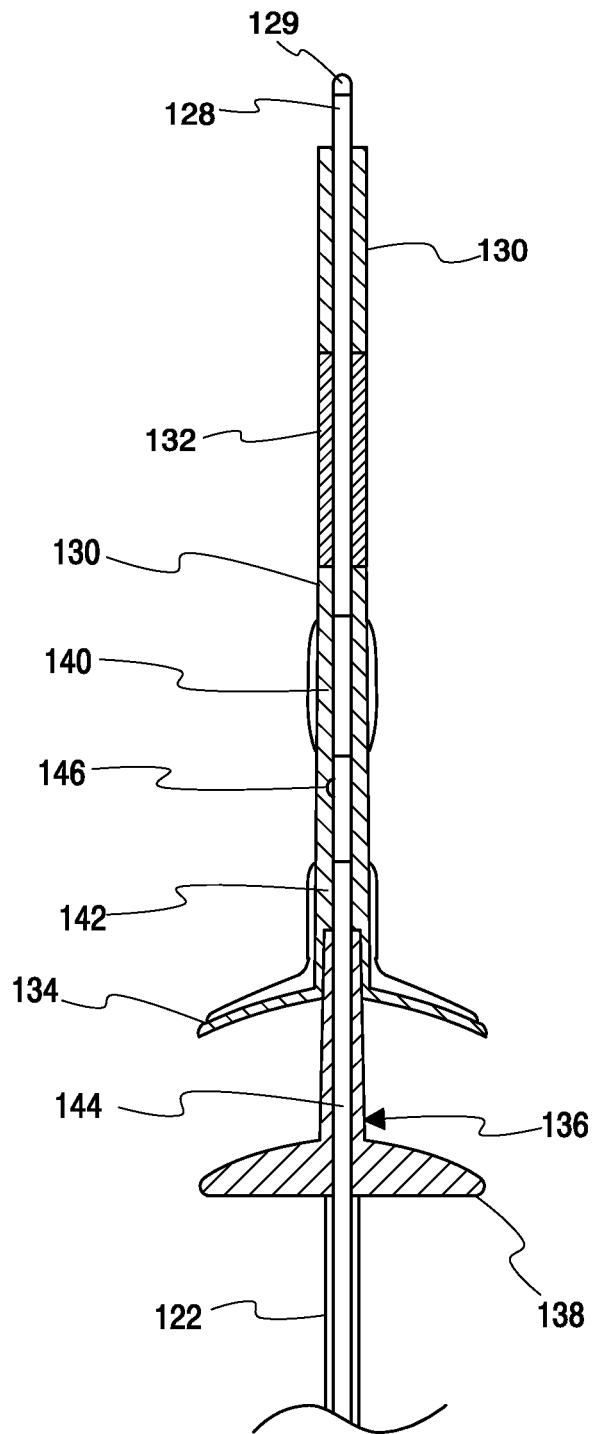
FIG. 15 is a diagrammatic section view of the barrel and plunger of the rectal catheter of FIG. 13.

FIGS. 13-15 illustrate details of an alternate auto retention irrigation catheter 112 for use with the system 100 in place of the body interface 102. The catheter 112 may be provided on a syringe-like device with a fluidly-isolated central conduit or tube extending therethrough. With reference to FIGS. 13 and 14, exterior portions of the catheter 112 can be seen. Starting at the proximal end (i.e., the end that enters the rectum), there is visible on the exterior a hollow tip 128, a barrel 130 (visible through the translucent outer balloon 114), a spacer sleeve 132 which surrounds the barrel, the barrel 130 again (visible this time through the translucent inner balloon 116), a flange 134, a plunger 136 and a press pad 138 affixed to the plunger. The outer balloon 114 may be sealed at its proximal end to one or both of the tip 128 and barrel 130, while the distal end of the outer balloon may be sealed to one or both of the barrel 130 and sleeve 132. Similarly, the inner balloon 116 may be sealed at its proximal end to one or both of the sleeve 132 and barrel 130, while the distal end of the inner balloon 116 may be sealed to one or both of the barrel and flange 134. The hollow interior of the tip 128 may communicate with the exterior via one or more radial ports, one of which can be seen at 129.

Looking now at FIG. 15, the internal construction of the irrigation catheter 112 can be seen. Note that for clarity the tip 128 and sleeve 132 are not shown in FIG. 15. The barrel 130 may be a hollow conduit with radial ports 140 and 142 through its outer wall. The ports 140, 142 may be axially located such that they are aligned with the inner and outer balloons 116 and 114, respectively. The flange 134, which may be integrally formed on the exterior of the barrel, may be mounted to the distal end of the barrel 130. The proximal end of the barrel 130 may include in its interior a central conduit or tube 144. Conduit 144 may provide a flow path through the barrel 130. The proximal end of the barrel 130 may be sealed so fluid cannot escape from an annulus 146 surrounding the conduit 144 within the barrel 130. The proximal end of the conduit 144 may also be sealed to the barrel 130 so that water cannot flow from the conduit 144 into the annulus 146 and the interior of the conduit 144. However, the interior of the conduit 144 may open to the exterior of the barrel 130. Water or other irrigating liquid can flow through the conduit 144 to the hollow tip 128. The central conduit 144 may be removably connectable at its distal end to the first irrigation tube 122.

The plunger 136 may have a hollow shaft 150 which preferably fits snugly into the annulus 146 between the barrel 130 inside wall and the outside wall of the conduit 144. The annulus 146 may be filled with a fluid, such as air, water or oil. This fluid may be used to inflate the balloons 114, 116. The distal end of the shaft 150 may carry the press pad 138. Due to the tight fit between the shaft 150 and the barrel 130, when a user draws the press pad 138 and shaft 150 into the barrel, fluid is forced out of the annulus 146, through the ports 140, 142 and into the balloons 114, 116, thereby inflating the balloons as noted by the arrows B in FIG. 14. This will remove the need for pumping and inflation of the balloons and the user may load/deploy the balloons after inserting the end of the device into the body before use.

Figure 17:
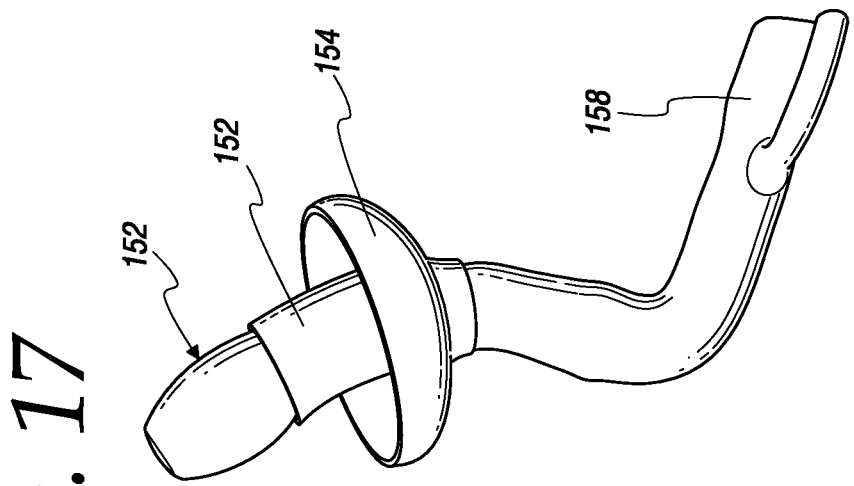
FIG. 17 is a perspective view of a further embodiment of a rectal catheter, which includes an inflationless cuff.
Figure 16:
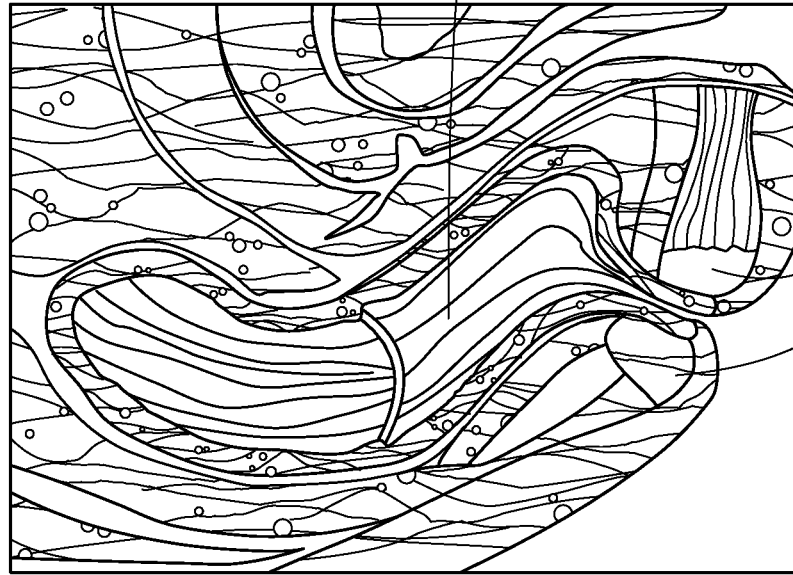
FIG. 16 is a cross-section of a human rectum and anus.
Figure 18:
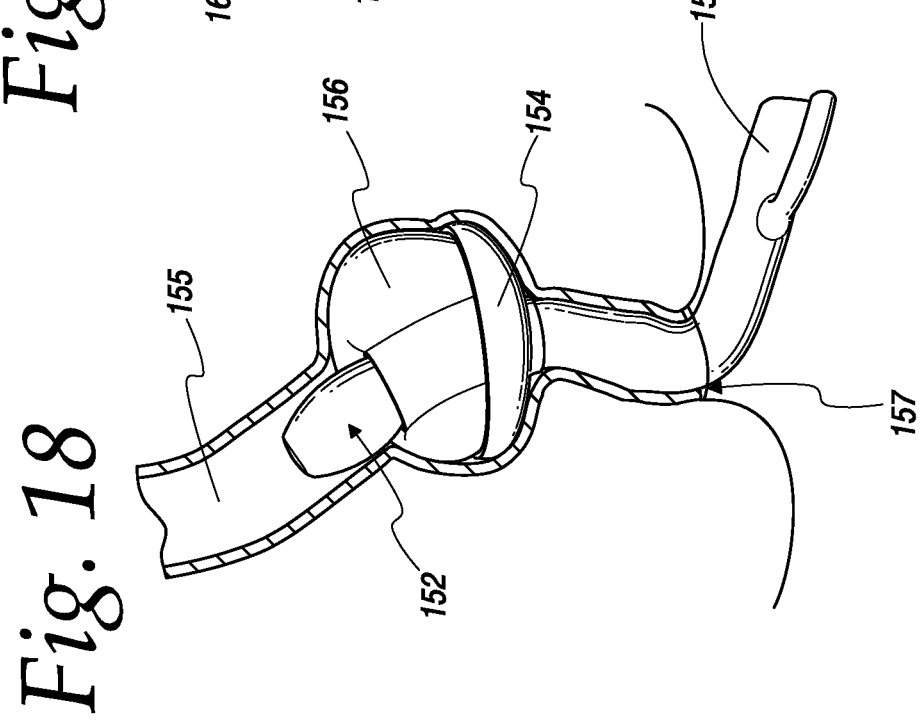
FIG. 18 is sectional view of the catheter of FIG. 17 deployed in a rectum.

FIGS. 16-18 show an anatomically-shaped catheter 152 having an inflationless cuff 154 that may be similar to the cuffs 40 and 76. Cuff 154 is made of soft, flexible material, such as silicone. Catheter 152 also has an inflatable cuff or balloon 156 located toward the proximal end relative to the inflationless cuff 154. The balloon is shown in its deflated condition in FIG. 17. FIG. 18 shows the catheter inserted in a user's rectum 155 with the balloon deployed to retain the catheter in the rectum. FIG. 18 also shows that the non-inflatable cuff 154 is deployed inside the anal sphincter 157. In this position the cuff can prevent leaks. The barrel 158 of the catheter may be mountable in a seat (not shown) similar to the seat 30 of FIG. 8. The seat may be connected to a waste collection bag such as bag 62 shown previously.

Figure 20:
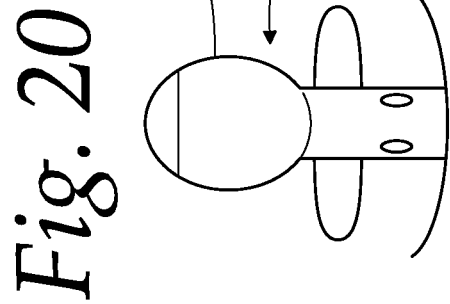
FIG. 20 is a sketch of a further alternate rectal catheter.
Figure 19:
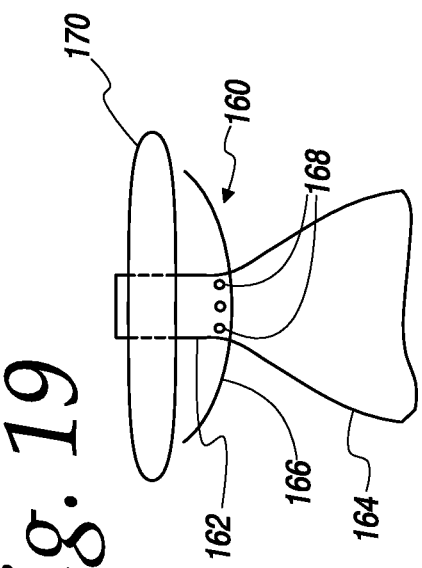
FIG. 19 is a sketch of an alternate rectal catheter.
Figure 21:
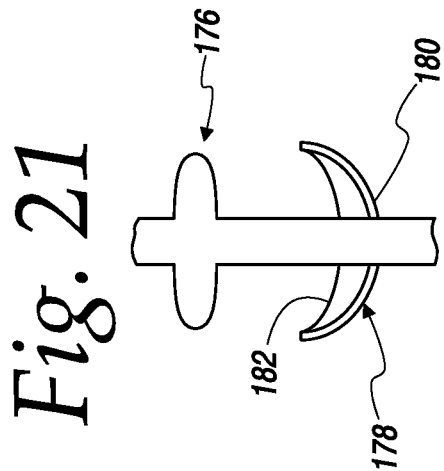
FIG. 21 is a sketch of yet another alternate rectal catheter.

FIG. 19 shows a variant of the catheter embodiments shown above. Here the catheter 160 has a proximal portion 162 that has a constant diameter (akin to that of a pediatric catheter), where it would then meet a tapered section 164 which would incorporate an inflationless cuff 166. There would be drainage holes 168 at this transition portion of the constant diameter with the tapered section 164, to minimize the volume of residual fecal matter retained within the inflationless cuff 166. The proximal portion of the catheter also incorporates a large volume balloon 170, disc-shaped, to aid retention in a flaccid bowel. A further variant of this is shown in FIG. 20, where the proximal end of the catheter 172 has a rounded geometry 174 to minimize the insertion force. FIG. 21 shows another alternative catheter 176 that has a hollow inflationless cuff 178 having a thick lower web 180 and a thin upper web 182.

It should be understood that various changes and modifications to the presently preferred embodiments described herein will be apparent to those skilled in the art. Such changes and modification can be made without departing from the spirit and scope of the invention disclosed herein.

The invention claimed is:

1. A rectal catheter irrigation system comprising:
   a catheter having a barrel with an insertion tip at a proximal end thereof, the barrel defining at least one lumen therein and at least one port communicating with the at least one lumen and the exterior of the barrel;
   a twist valve at a distal end of the barrel, the twist valve having an internal section and pathway, the twist valve being in fluid communication with the at least one lumen and selectably twistable between open and closed positions which permit and prevent, respectively, fluid flow out of the at least one lumen at the distal end of the barrel, when twisted to the open position the twist valve opens the internal section and pathway, allowing waste water to flow through the at least one lumen;
   a collection bag connected at the distal end of the barrel; and
   a connector attached to the barrel intermediate the twist valve and the at least one port, the connector having a passage in fluid communication with the at least one lumen and being capable of connection to an irrigation fluid reservoir.

2. The system of claim 1 further comprising an inflationless cuff attached to the exterior of the barrel, the cuff being made of a flexible material.

3. The system of claim 1 wherein the barrel includes an opening at a distal most end of the distal end of the barrel.

4. The system of claim 3 further including the collection bag directly connected to the opening at the distal most end of the distal end of the barrel.

5. The system of claim 1 further comprising an irrigation fluid reservoir and fluid supply tubing in fluid communication with the irrigation fluid reservoir and the connector of the barrel.

6. The system of claim 5 further comprising a controller in the fluid supply tubing for controlling flow from the irrigation fluid reservoir to the catheter.

7. The system of claim 5 further comprising a pump associated with the irrigation fluid reservoir for pumping fluid from the irrigation fluid reservoir to the catheter.

8. The system of claim 1 further comprising retention straps connected to the collection bag.

9. The system of claim 1 further comprising an inflationless cuff attached to the exterior of the barrel, the cuff being made of a material sufficiently flexible to permit insertion of the inflationless cuff into the rectum where it seals against leakage around the exterior of the barrel.

10. The system of claim 9 further comprising an inflatable balloon attached to the exterior of the barrel.

11. The system of claim 10 wherein the inflatable balloon is attached closer to the insertion tip than is the inflationless cuff.

* * * * *